United States Patent [19]
Marks et al.

[11] Patent Number: 5,910,583
[45] Date of Patent: Jun. 8, 1999

[54] ANTISENSE OLIGONUCLEOTIDES AGAINST ERBB-2

[75] Inventors: Jeffrey R. Marks, Hillsborough; James P. Vaughn; James D. Inglehart, both of Durham, all of N.C.

[73] Assignee: Duke University, Durham, N.C.

[21] Appl. No.: 08/740,821

[22] Filed: Nov. 4, 1996

[51] Int. Cl.[6] .............................. C07H 21/04; C12Q 1/68
[52] U.S. Cl. .................... 536/24.5; 536/23.1; 536/24.31; 435/6; 435/91.1; 435/375
[58] Field of Search ........................... 435/6, 91.1, 172.1, 435/172.3, 325, 366; 536/23.1, 24.1, 24.5; 514/44, 24.31

[56] References Cited

U.S. PATENT DOCUMENTS 5,599,704  2/1997  Thompson et al. ...................... 435/325

FOREIGN PATENT DOCUMENTS

95/17507  6/1995  WIPO .

OTHER PUBLICATIONS

Vaughn et al., "Antisense DNA downregulation of the ERBB2 oncogene measured by a flow cytometric assay", *Proc. Natl. Acad. Sci. USA* 92:8338–8342, Aug. 1995.
Mahen et al. Archives of Biochem. & Biophys. 253:214–220, 1987.
Gewirtz et al. PNAS 93:3161–3163 (1996).
Rojanasakul Adv. Arug. Delivery Ruvs. 18(1996) 115–131.

*Primary Examiner*—John LeGuyader
*Attorney, Agent, or Firm*—Myers Bigel Sibley & Sajovec

[57] ABSTRACT

Oligonucleotides consisting of the nucleotide sequence US-3 [GGT GCT CAC TGC GGC (SEQ ID NO:2)] or UT-1 [TGC GGC TCC GGC CCC (SEQ ID NO:5)]. The oligonucleotides are useful as antisense oligonucleotides for inhibiting the expression of the ERBB2 tyrosine kinase receptor in a cell, in vitro or in vivo.

3 Claims, 6 Drawing Sheets

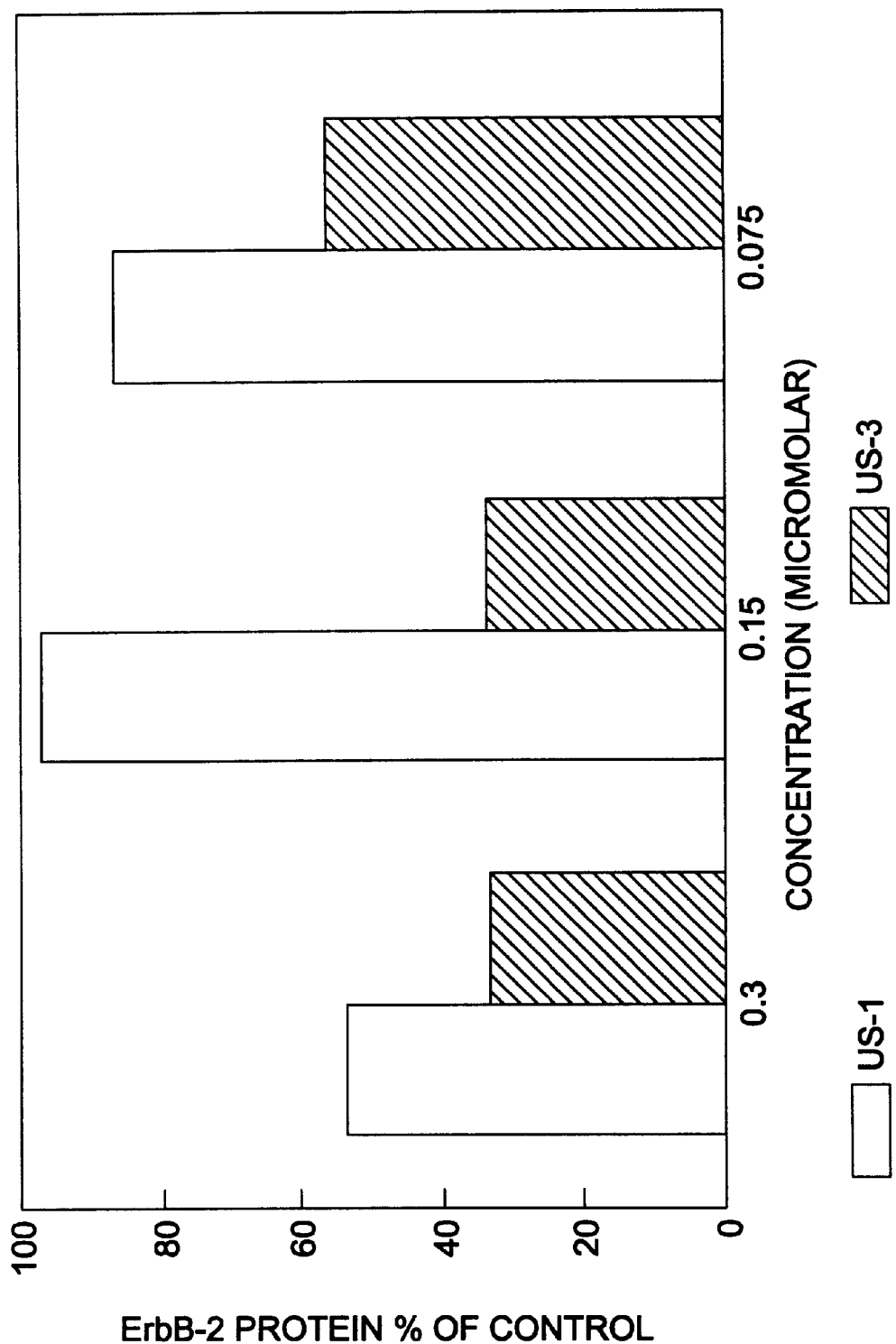

ANTISENSE OLIGONUCLEOTIDES AGAINST ERBB-2

This invention was made with Government support under Grant No. UO1-CA60139 from the National Cancer Institute. The Government has certain rights to this invention.

FIELD OF THE INVENTION

The present invention relates to antisense oligonucleotides in general, and particularly relates to antisense oligonucleotides that downregulate the ERBB2 oncogene.

BACKGROUND OF THE INVENTION

Antisense oligonucleotides have long held the potential to decrease the expression of a targeted gene by inhibiting transcription or translation and thereby achieve a phenotypic effect based upon the expression of that gene. However, many of the effects achieved by these oligonucleotides may not be mediated by inhibition of the target gene (C. Stein and Y.-C. Cheng, Science 261, 1004–1012 (1993); R. Wagner, Nature 372, 333–335 (1994)).

The erbB-2 gene codes for a 185kd tyrosine kinase linked transmembrane protein which is overexpressed in 30–50% of primary breast cancers (D. Slamon et al., Science. 244, 707–712 (1989); M. Press et al., Prog. Clin. Biol. Res. 354A, 209–221 (1990); M. Berger et al., Cancer. Res. 48, 1238–1243 (1988); D. Allred et al., Hum. Pathol 23, 974–979 (1992)). Overexpression, which is frequently due to gene amplification, is an early event in the development of many breast cancers and is maintained during invasion and metastatic progression of the disease (J. D. Iglehart et al., Cancer. Res. 50, 6701–6707 (1990)). Expression of erbB-2 is low in most normal adult tissues making it an attractive therapeutic target (M. Press et al., Oncogene. 5, 953–962 (1990)). We recently described a set of methods for delivering phosphorothioate oligonucleotides and measuring antisense activity against the human erbB-2 oncogene in breast cancer cells (J. Vaughn et al., Proc. Natl. Acad. Sci. U. S. A. 92, 8338–8342 (1995)). Antisense oligonucleotides or control sequences are co-delivered to cells with a fluorescent tagged oligonucleotide using cationic liposome mediated transfer. A high concentration of the fluorescent tracer and non-tagged oligonucleotide rapidly accumulate in the nucleus. Cells receiving the co-delivered oligonucleotides can then be identified, quantitated, immunostained for the level of the antisense target protein, and physically sorted to measure RNA levels and phenotypic changes. Because flow cytometric analysis is quantitated on a per cell basis, simultaneous two-color analysis of the tagged oligonucleotide (a measure of dose) versus immunodetection of the targeted gene product yields a dose-response curve for a given antisense compound.

An object of this invention is to develop antisense compounds targeted to the erbB-2 oncogene, which is amplified and overproduced in a large fraction of breast and other epithelial cancers.

SUMMARY OF THE INVENTION

A first aspect of the present invention is an oligonucleotide that downregulates the ERBB2 oncogene, such as an oligonucleotide consisting of the nucleotide sequence US-3 [GGT GCT CAC TGC GGC (SEQ ID NO:2)] or UT-1 [TGC GGC TCC GGC CCC (SEQ ID NO:5)].

A second aspect of the present invention is a method of inhibiting the expression of the ERBB2 tyrosine kinase receptor in a cell, comprising administering to said cell an antisense oligonucleotide as described above.

A third aspect of the present invention is a method of treating a cancer in a subject in need of such treatment, comprising administering to said subject an effective cancer-treatment amount of an antisense oligonucleotide as given above.

The foregoing and other objects and aspects of the present invention are discussed in detail in the drawings herein and the specification set forth below.

BRIEF DESCRIPTION OF THE DRAWINGS

FIG. 1: Two-color flow cytometric analysis of antisense inhibition of erbB-2 protein using different phosphorothioate and phosphorodithioate backbones. The indicated oligonucleotides together with a fluorescein labeled tracer oligonucleotide were co-delivered to SK-BR-3 cells via cationic liposomes. Cells were cultured for 48 hours and then immunostained for cell surface erbB-2 protein using the monoclonal antibody, TA-1, and a R-phycoerythrin conjugated secondary antibody. The cells were then analyzed simultaneously for the level of fluorescein and phycoerythrin. The US-1 antisense (SEQ. ID NO:1) and US-D (SEQ. ID NO:6) scrambled control were used in the following configurations: S; all monothioate linkages, SO; alternating monothio and phosphodiester linkages, S-CAP; 3 monothioate linkages at each end of the 15 base sequence, S2-CAP; 3 dithioate linkages at each end, and S2O2; alternating dithioate linkages.

FIG. 5: Dose response comparison of US-1 (SEQ ID NO:1) versus US-3 (SEQ ID NO:2) in inhibiting de novo erbB-2 protein synthesis. Specifically immunoprecipitating bands were quantitated by phosphorimage analysis and the erbB-2 signal was normalized to PCNA in each lane. The downregulation at each dose is measured as a percentage of erbB-2 protein in the antisense treated cultures compared to the cognate control at each dose.

DETAILED DESCRIPTION OF THE INVENTION

Figure 1A:
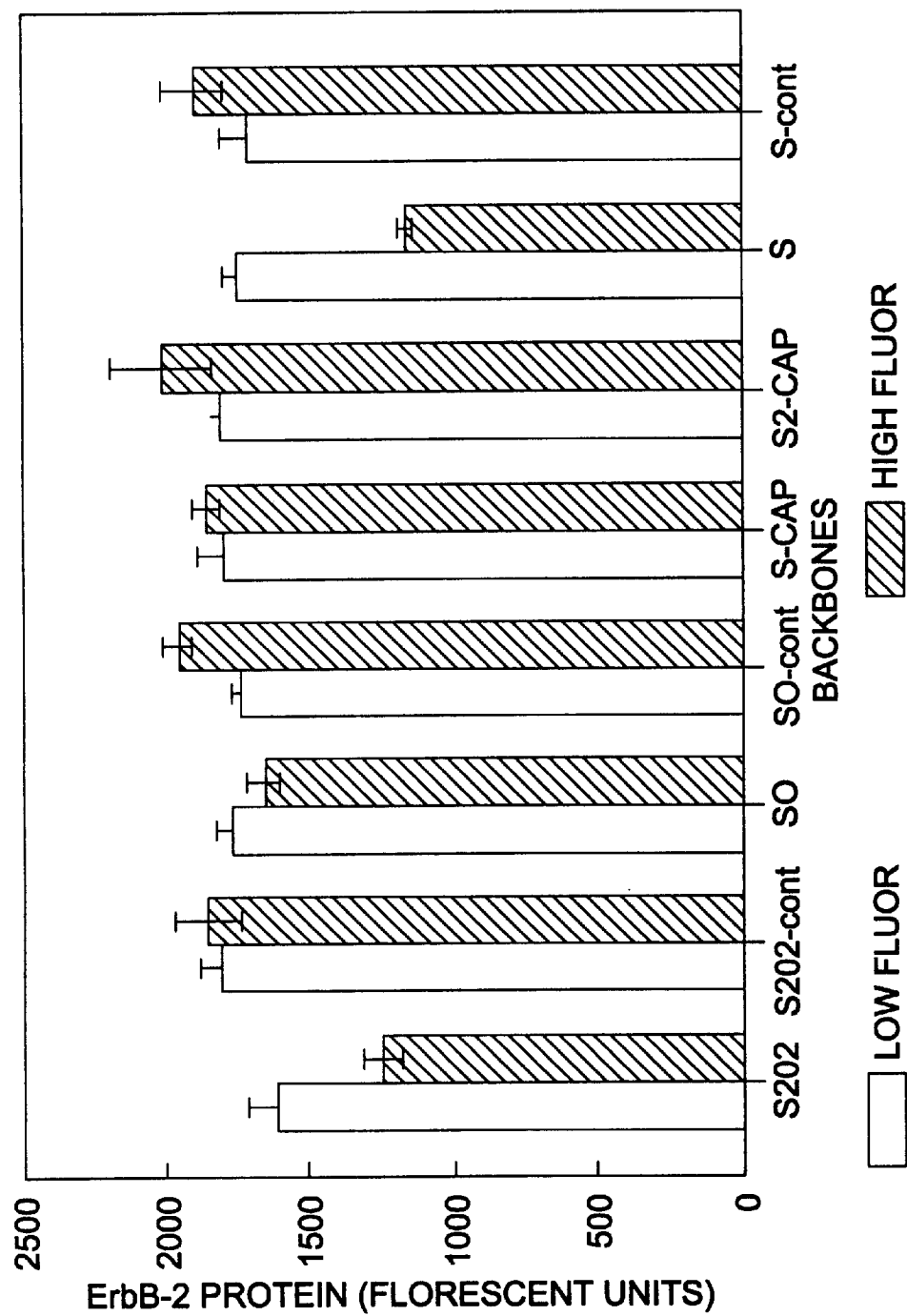
FIG. 1A: Quantitation of erbB-2 inhibition in triplicate cultures. Mean erbB-2 levels were calculated in the high and low fluorescent tracer windows.

Antisense oligonucleotides can be made in accordance with known techniques. See, e.g., U.S. Pat. No. 5,149,797 to Pederson et al. (The disclosures of all patent references cited herein are to be incorporated herein by reference). Antisense oligonucleotides may be deoxyribonucleotide or ribonucleotide sequences. Numerous antisense oligonucleotide backbone chemistries are known. For example, such oligonucleotides may be oligonucleotides wherein at least one, or all, of the internucleotide bridging phosphate residues are modified phosphates, such as methyl phosphonates, methyl phosphonothioates, phosphorothioates, phosphoromorpholidates, phosphoropiperazidates, propynes, phosphoramidates, and alkylphosphotriesters. See generally P. Ts'o et al., Ann. *N. Y. Acad. Sci.* 507, 220–241 (1987), C. Stein et al., *Nucleic. Acids. Res.* 16, 3209–3221 (1988), R. Wagner et al., *Science.* 260, 1510–1513 (1993), B. Froehler et al., *Nucleic. Acids. Res.* 16, 4831–4839 (1988), K. Gallo et al., *Nucleic. Acids. Res.* 14, 7405–7420 (1986). For example, every other one of the internucleotide bridging phosphate residues may be modified as described.

In another example, such antisense oligonucleotides are oligonucleotides wherein at least one, or all, of the nucleotides contain a 2' loweralkyl moiety (e.g., C1–C4, linear or branched, saturated or unsaturated alkyl, such as methyl, ethyl, ethenyl, propyl, 1-propenyl, 2-propenyl, and isopropyl) . For example, every other one of the nucleotides may be modified as described. See also P. Furdon et al., *Nucleic Acids Res.* 17, 9193–9204 (1989); S. Agrawal et al., *Proc. Natl. Acad. Sci. USA* 87, 1401–1405 (1990); C. Baker et al., *Nucleic Acids Res.* 18, 3537–3543 (1990); B. Sproat et al., *Nucleic Acids Res.* 17, 3373–3386 (1989); R. Walder and J. Walder, *Proc. Natl. Acad. Sci. USA* 85, 5011–5015 (1988).

Those skilled in the art will appreciate that minor modifications may be made to the oligonucleotides disclosed herein. In general, antisense oligonucleotides are preferably 13 to 18 nucleotides in length, more preferably 14 to 16 or 17 nucleotides in length, and most preferably 15 nucleotides in length. In addition, the sequences may be made shorter or longer on the 3' or 5' ends thereof. For example, with reference to FIG. 3 and Table 1 herein, an oligonucleotide of the invention may any continuous fragment of a length as given above, of the antisense (top) strand shown in the FIG. 3, from nucleotide 148, 149, 150 or 151 to nucleotide 174, 175, 176 or 177.

The term "anti-sense oligonucleotide" includes the physiologically and pharmaceutically acceptable salts thereof: i.e., salts that retain the desired biological activity of the parent compound and do not impart undesired toxicological effects thereto. Examples of such salts are (a) salts formed with cations such as sodium, potassium, $NH_4^+$, $NX_4^+$ wherein X is a $C_{1-4}$ alkyl group, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (d) salts formed from elemental anions such as chlorine, bromine, and iodine; etc.

Formulations of the present invention comprise the antisense oligonucleotide in a physiologically or pharmaceutically acceptable carrier, such as an aqueous carrier.

Thus, formulations for use in the present invention include, but are not limited to, those suitable for parenteral administration, including subcutaneous, intradermal, intramuscular, intravenous and intraarterial administration, as well as topical administration. The formulations may conveniently be presented in unit dosage form and may be prepared by any of the methods well known in the art. The most suitable route of administration in any given case may depend upon the subject, the nature and severity of the condition being treated, and the particular active compound which is being used.

The present invention provides for the use of antisense oligonucleotides having the characteristics set forth above for the preparation of a medicament for carrying out the methods described herein. In the manufacture of a medicament according to the invention, the antisense oligonucleotide is typically admixed with, inter alia, an acceptable carrier. The carrier must, of course, be acceptable in the sense of being compatible with any other ingredients in the formulation and must not be deleterious to the patient. The carrier may be a solid or a liquid. One or more antisense oligonucleotides may be incorporated in the formulations of the invention, which may be prepared by any of the well known techniques of pharmacy consisting essentially of admixing the components, optionally including one or more accessory therapeutic ingredients.

Formulations of the present invention may comprise sterile aqueous and non-aqueous injection solutions of the active compound, which preparations are preferably isotonic with the blood of intended recipient and essentially pyrogen free. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use.

In the formulation the antisense oligonucleotide may be contained within a lipid particle or vesicle, such as a liposome or microcrystal, which may be suitable for parenteral administration. The particles may be of any suitable structure, such as unilamellar or plurilamellar, so long as the antisense oligonucleotide is contained therein. Positively charged lipids such as N-[1-(2,3-dioleoyloxi) propyl] -N,N,N-trimethyl-amoniummethylsulfate, or "DOTAP," are particularly preferred for such particles and vesicles. The preparation of such lipid particles is well known. See, e.g., U.S. Pat. Nos. 4,880,635 to Janoff et al.; 4,906,477 to Kurono et al.; 4,911,928 to Wallach; 4,917,951 to Wallach; 4,920,016 to Allen et al.;4,921,757 to Wheatley et al.; etc.

The dosage of the antisense oligonucleotide administered will depend upon the particular method being carried out, and when it is being administered to a subject, will depend on the disease, the condition of the subject, the particular formulation, the route of administration, etc. In general, intracellular concentrations of the oligonucleotide of from 0.05 to 50 µM, or more particularly 0.2 to 5 µM, are desired. For administration to a mammalian subject such as a human, a dosage of from about 0.01, 0.1, or 1 mg/Kg up to 50, 100, or 150 mg/Kg is employed.

The oligonucleotides and formulations of the present invention have a variety of uses. The oligonucleotides of the invention may be used in a method of inhibiting the expression of the ERBB2 tyrosine kinase receptor in a cell, in vitro or in vivo, the method comprising administering to said cell an antisense oligonucleotide consisting of the nucleotide sequence US-3 or NT-1. The cell may be an epithelial cell, or any cell that overexpresses the ERBB2 tyrosine kinase receptor (e.g., a tumor cell). The cell may be selected from the group consisting of breast cancer, ovarian cancer, lung cancer, and colon cancer cells. The method may be carried out in vivo on a subject in need of such treatment, as discussed in further detail below, or may be carried out in vitro in a process for identifying compounds that inhibit the overexpression of the ERBB2 tyrosine kinase receptor, as described in J. Vaughn et al., *Proc. Natl. Acad. Sci. USA* 8338–8342 (1995).

The oligonucleotides may be used to carry out a method of treating cancer in a subject in need of such treatment. Subjects to be treated include both human subjects and animal subjects for veterinary purposes (e.g., dog, cat), but are preferably mammalian subjects. The method comprises administering to the subject an effective cancer-treatment amount (e.g., an amount sufficient to delay the progress of the disease) of an antisense oligonucleotide as described herein. Cancers that may be treated by the method of the present invention are, in general, epethelial cell cancers, or any cancer in which the cancer cells overexpress the ERBB2 tyrosine kinase receptor. Particular cancers that may be treated by the method of the present invention include breast cancer, ovarian cancer, lung cancer, and colon cancer. The administering step may be carried out by any suitable means, as discussed above, including but not limited to intraveneous, intraarterial, intramuscular, subcutaneous, and intraperitoneal injection.

The oligonucleotides of the present invention may be used for a variety of other purposes, as will be appreciated by those skilled in the art. For example, the oligonucleotides may be labelled with a suitable detectable group (a radioisotope, a ligand, another member of a specific binding pair) and used as hybridization probes to detect the ERBB2 gene; the molecular weights of the oligonucleotides may be determined and the oligonucleotides used as molecular weight markers, etc.

The present invention is explained in greater detail in the following non-limiting examples. Nucleotide sequences are presented herein by single strand only, in the 5' to 3' direction, from left to right, unless otherwise indicated.

EXAMPLE 1

Oligonucleotide Synthesis

Antisense and scrambled control phosphorothioate and phosphorodithioate oligonucleotides were synthesized on an ABI 380B DNA synthesizer (Perkin Elmer) as previously described (G. Beaton et al., in *Oligonucleotides and their analogues, A practical approach* pp. 109–135, (F. Eckstein ed. 1991); G. Beaton et al., *Tetrahedron* 47, 2377–2388 (1991)). After synthesis, oligomers were purified by HPLC and purity was ensured by collection of a single peak. $^{31}$P-NMR was performed on all syntheses to verify that thio or dithio linkages were greater than 95% of the total. A fluorescein 5' end-labeled phosphorothioate oligomer (Tracer) was obtained from Research Genetics. Oligomers were diluted to a concentration of 20 µM, filter sterilized, and stored frozen in distilled water. We have observed no evidence of degradation or loss of antisense activity with oligomers stored in this way over the course of a 10 month period.

EXAMPLE 2

Cell Culture and Liposome Mediated Delivery

SK-BR-3 cells were obtained from the American Type Culture Collection and maintained in RPMI 1640 containing 10% heat inactivated fetal bovine serum (FBS). For liposome delivery, cells were preincubated in serum free medium (Opti-Mem I, Gibco/BRL). For a typical experiment, oligonucleotides were added to Lipofectin (Gibco/BRL) yielding final concentrations of 0.3 µM test oligomer, 0.05 µM fluorescein oligomer, and 10 µg/ml Lipofectin. Liposome-oligomer solutions were incubated for 30 minutes at room temperature and then added at a volume of 0.3 ml per 16 mm tissue culture well. Cells were incubated with the liposome solution for 4 hours after which RPMI containing 10% FBS was added to stop uptake of liposomes.

EXAMPLE 3

ErbB-2 Protein Detection and Flow Cytometry

Immunofluorescent detection of cell surface receptors was performed as previously described (J. Vaughn et al., *Proc. Natl. Acad. Sci. U. S. A.* 92, 8338–8342 (1995)). Briefly, cells were treated with 0.25% trypsin/1 mM EDTA, counted, and aliquoted at approximately 50,000/well into 96-well plates. Cells were pelleted at 2000×g at 5° C., washed two times in ice cold azide wash buffer (PBS, 0.5%FBS, 0.1% azide) and then resuspended in 100 µl of 1% bovine serum albumin (BSA) containing the erbB-2 mouse monoclonal, TA-1 (oncogene Science) at 0.25 µg/ml. Cells were incubated on ice for 1 hour, washed three times in azide wash buffer, then incubated on ice in 1% BSA containing the R-phycoerythrin labeled goat anti-mouse conjugated (Molecular Probes) secondary antibody at 10 µg/ml for 1 hour. Cells were washed and then analyzed by flow cytometry on a Becton Dickinson FACStar Plus. For physically sorting populations, cells were trypsinized, pelleted, and brought up to a final concentration of 2×10$^6$/ml in RPMI plus 20% FBS then sorted by fluorescein content in a Becton Dickinson FACStar Plus flow cytometer at an average flow rate of 2000 cells/second.

EXAMPLE 4

Northern Blotting

After sorting cells based upon the level of the fluorescent tracer, total RNA was extracted by the guanidium thiocyanate method (P. Chomczynski and N. Sacchi, *Anal. Biochem.* 162, 156–159 (1987)). RNA was electrophoresed, blotted, and probed for erbB-2 as previously described (J. Marks et al., *J. Virol.* 63, 790–797 (1989)). Densitometry of short exposure autoradiograms was performed to quantitate the amount of hybridization.

EXAMPLE 5

Immunoprecipitation

Radioimmunoprecipitations were performed as previously described (A. Davidoff et al., Proc. Natl. Acad. Sci. U. S. A. 89, 3439–3442 (1992)). Briefly, cells were treated with oligomers complexed with cationic liposomes and then labeled with 50 $\mu$Ci/ml of $^{35}$S-methionine in methionine free RPMI for 3 hours. Extracts were prepared by NP-40 lysis and sonication and protein concentrations quantitated by the Bradford Assay (BioRad). Equal amounts -of protein were precleared with protein G Sepharose (Pharmacia) and then reacted with a combination of 1 $\mu$g of anti-erbB-2 (TA-1, Oncogene Science) and 1 $\mu$g of anti-PCNA (Dako) monoclonal antibodies. The immune complexes were recovered by binding to protein G Sepharose, washed, boiled in SDS-sample buffer, and then electrophoresed on 7.5% SDS-PAGE. Gels were fixed, dried, and the signals quantitated by analysis on a Molecular Dynamics Phosphorimager. The negative control for immunoprecipitation was performed with 2 $\mu$g/ml of mouse IgG (Coulter Immunology). Results were reported as a ratio between the erbB-2 and PCNA signals.

EXAMPLE 6

Antisense Effects by Variations of the Thioated Backbone

We previously identified a lead sequence for downregulating the erbB-2 oncogene in the SK-BR-3 human breast cancer cell line (J. Vaughn et al., Proc. Natl. Acad. Sci. U. S. A. 92, 8338–8342 (1995)). The erbB-2 gene is amplified in this cell line by approximately 16 fold and the protein is overexpressed compared to normal mammary epithelial cells by a factor of approximately 100 (M. Kraus et al., EMBO. J. 6, 605–610 (1987)). This sequence targets the AUG initiation codon of the erbB-2 gene and has been designated US-1 (SEQ ID NO:1; Table 1). We have used a scrambled US-1 sequence (SEQ ID NO:1) as a specific control for this compound, designated US-D (SEQ ID NO:6). The US-1 (SEQ ID NO:1) sequence was synthesized with the following configurations for antisense testing (Table 2): 1) All phosphoromonothioate linkages (S), 2) All phosphorodithioate linkages (S2), 3) Alternating monothio and phosphodiester linkages (SO), 4) Alternating dithio and phosphodiester linkages (S2O2), 5) Three monothioate linkages at the 5' and 3' ends and phosphodiester linkages in the middle (capped monothios, S-CAP), and 6) Three dithio linkages at the 5' and 3' ends and phosphodiester linkages in the middle (capped dithios, S2-CAP). The US-D scrambled control sequence (SEQ ID NO:6) was also synthesized with all monothioate, all dithioate, alternating monothioate, and alternating dithioate configurations.

We tested the relative efficacy of these sequences for downregulating erbB-2 using a two-color flow cytometric assay (J. Vaughn et al., Proc. Natl. Acad. Sci. U. S. A. 92, 8338–8342 (1995)). This method takes advantage of co-delivery, via cationic liposome mediated transfection, of a tracer oligonucleotide that is fluoresceinated at the 5' end (SEQ ID NO:8, Table 1). This allows us to identify and quantitate cells that receive varying doses of the tracer and unlabeled antisense oligonucleotides. We have previously shown that treatment of these cells with cationic liposomes plus the fluorescent tracer oligonucleotide does not affect the level of erbB-2 cell surface protein (J. Vaughn et al., supra). Both by fluorescence microscopy and flow cytometry, we have observed that the tracer rapidly accumulates in the nucleus while very little fluorescence is associated with the cell membrane. The highest levels of nuclear fluorescence are observed shortly after the 4 hour liposome treatment. There is a steady decline in both the intensity and frequency of cells with nuclear fluorescence so that by 96 hours, few cells have detectable levels. While small oligonucleotides can rapidly diffuse into the nucleus of dead cells, the vast majority of cells treated in this manner with nuclear fluorescence are alive as determined by dye exclusion, their light scattering properties as measured by flow cytometry, and the continued viability of these cells after flow cytometric sorting. Most importantly, nuclear fluorescence coincided with erbB-2 downregulation at the protein and RNA level (J. Vaughn et al., supra).

TABLE 1

ERBB-2 SEQUENCES TESTED FOR ANTISENSE EFFICACY

| Name | Sequence | Location[1] |
|---|---|---|
| US-1 | CTC CAT GGT GCT CAC (SEQ ID NO: 1) | 166–180 |
| US-3 | GGT GCT CAC TGC GGC (SEQ ID NO: 2) | 160–174 |
| US-4 | CGC CAG CTC CAT GGT (SEQ ID NO: 3) | 173–187 |
| US-5 | CAA GGC CGC CAG CTC (SEQ ID NO: 4) | 178–192 |
| UT-1 | TGC GGC TCC GGC CCC (SEQ ID NO: 5) | 151–165 |
| US-D | CGC CTT ATC CGT AGC (SEQ ID NO: 6) | US-1 scrambled control |
| SC-3 | GGT CGA TGC CGC GTC (SEQ ID NO: 7) | US-3 scrambled control |
| Tracer | TCT CTC TCT CTT TTT (SEQ ID NO: 8) | fluoresceinated tracer |

[1]The initiating methionine for erbB-2 translation begins at base 175, Genbank Accession #X03363.

TABLE 2

DESCRIPTION OF US-1 (SEQ ID NO: 1) COMPOUNDS TESTED WITH DIFFERENT LINKAGES

| Name | Backbone Description |
|---|---|
| S | All monothioate linkages |
| S-CAP | Three monothioate linkages at 5' and 3' end, and phosphodiester linkages in the center |
| SO | Alternating monothioate and phosphodiester, with monothioate at the 5' and 3' ends |
| S2O2 | Alternating dithioate and phosphodiester, with dithioate at the 5' and 3' ends |
| S2-CAP | Three dithioate linkages at 5' and 3' end, with phosphodiester linkages in the center |
| S2 | All dithioate linkages |

The antisense compounds with different backbone configurations were delivered at a 6:1 ratio (antisense:tracer) to SK-BR-3 cells. After a 48 hour incubation, cell surface erbB-2 protein was detected by indirect immunofluorescence using an anti-erbB-2 monoclonal antibody. In the flow cytometric analysis of this experiment, significantly decreased erbB-2 protein levels were observed using only the full monothioate (US-1, SEQ ID NO:1;S) and the alternating dithioate (US-1 SEQ ID NO:1;S2O2) compounds. This is represented by the number of cells in the lower right quadrant of these two-dimensional plots, i.e., high levels of tracer and low levels of erbB-2. The alternating monothioate (SO) and both the capped mono and dithioate (S-CAP and S2-CAP) failed to reduce the levels of cell surface erbB-2 protein in this assay. Results from three separate experiments were quantitated and plotted in FIG. 1A. For this analysis, the level of erbB-2 protein was compared not only between different backbones but also between the high and low fluorescent fractions for each compound. Again, only the S and S2O2 US-1 (SEQ ID NO:1) compounds significantly downregulated the steady-state levels of erbB-2 protein in the high fluorescent fraction.

Figure 1B:
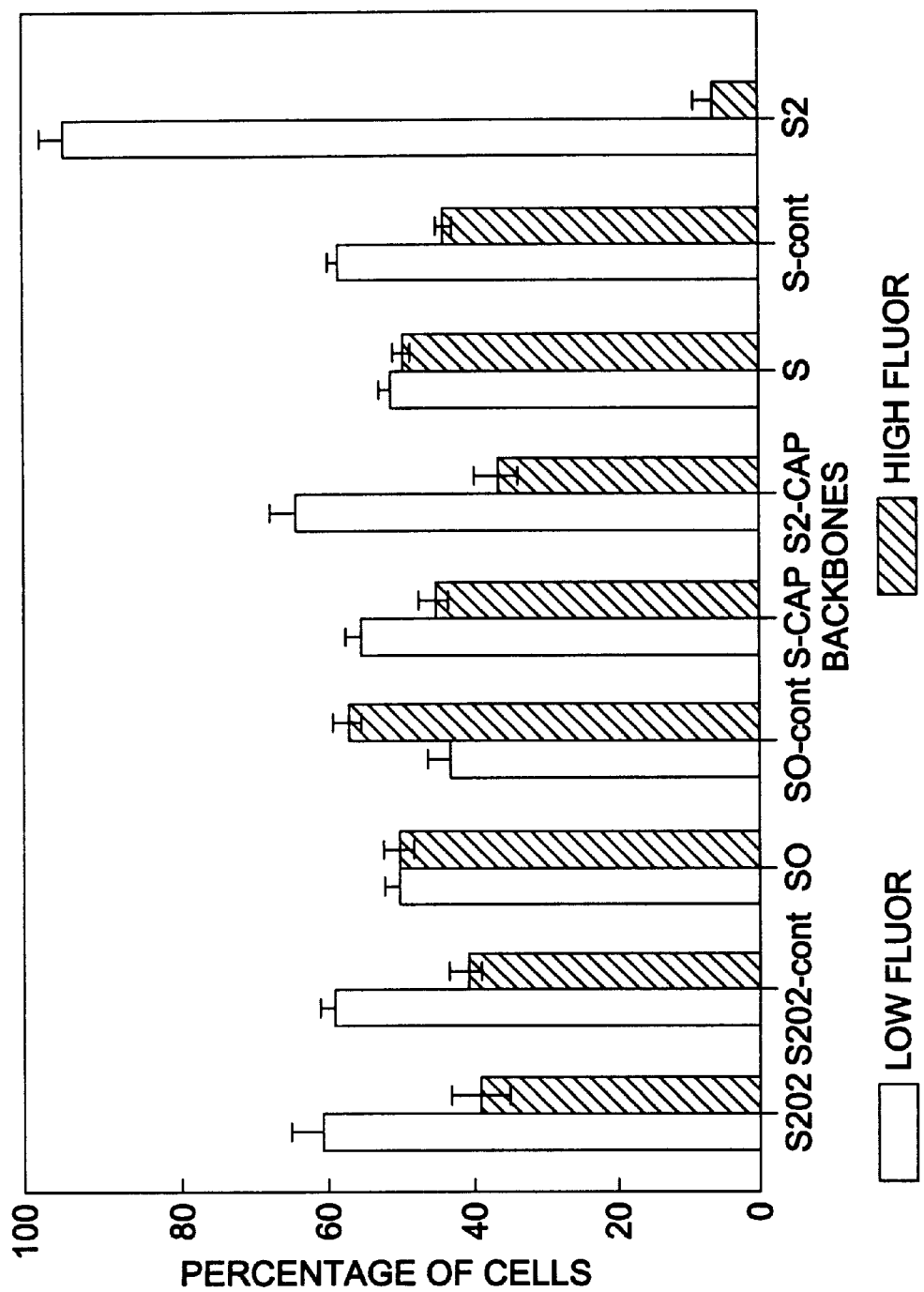
FIG. 1B: The mean percentage of cells that contained high and low levels of the fluorescent tracer at 48 hours after delivery.

The full dithioate compound (S2) was not effective using this method. In no instance did we observe intracellular accumulation of the tracer oligonucleotide or downregulation of erbB-2 using this compound (data not shown). This was reflected by the relative percentage of cells containing high or low levels of the tracer oligonucleotide (Figure 1B). Forty-eight hours after delivery of the different backbones, the percentage of cells containing over a threshold level of tracer (High Fluorescent), varied between 40–60% of the lipofected culture. In general, cells receiving monothioates contained higher levels of tracer oligonucleotide than those receiving dithioated DNA. However, there were virtually no cells that contained a significant level of fluorescence when co-lipofected with the S2 compound, even when the cells were examined immediately after the 4 hour lipofection procedure. Given this apparent failure of delivery, the full dithioate compounds were eliminated from further analysis in this study.

Figure 2:
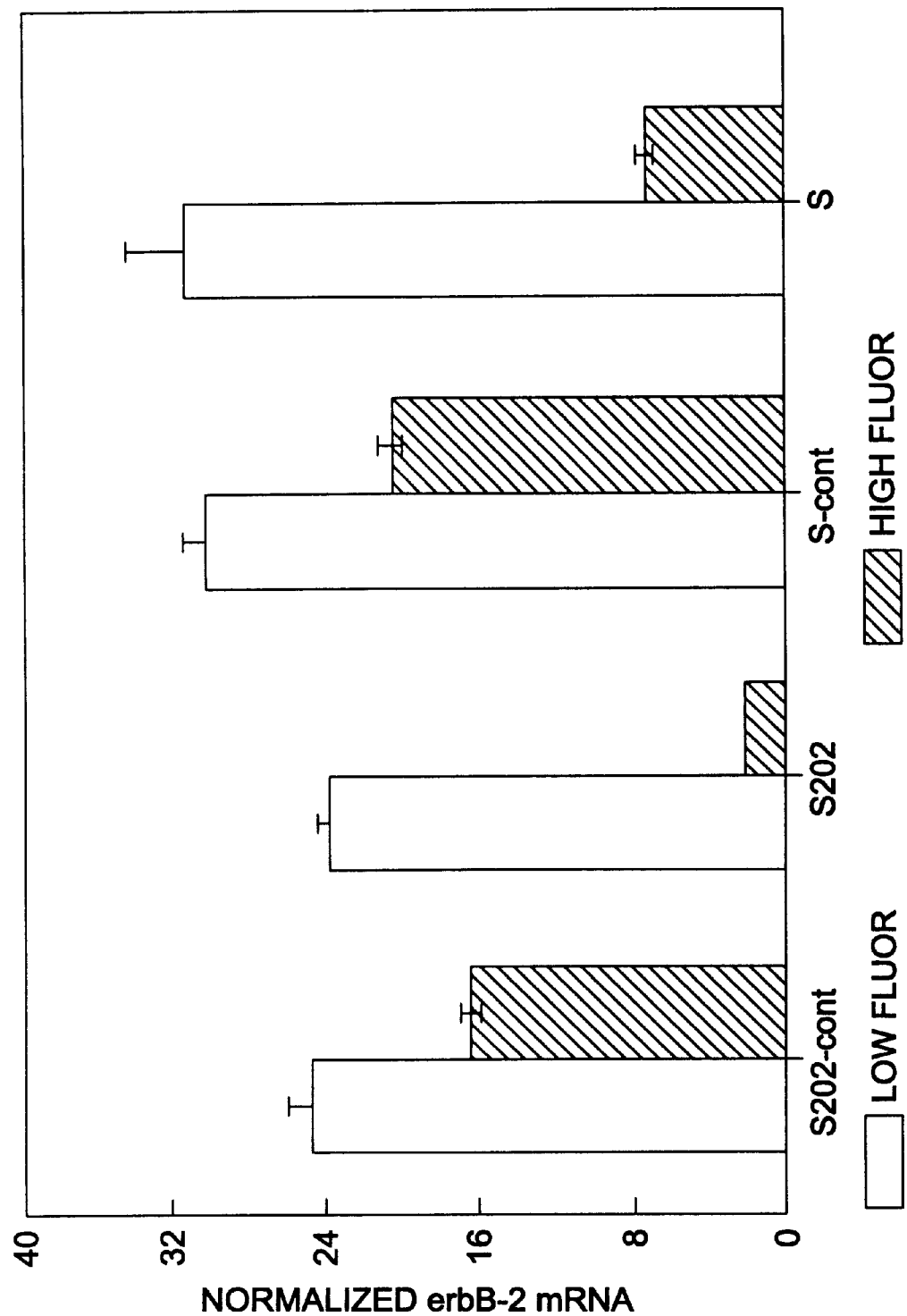
FIG. 2: Specific inhibition of erbB-2 mRNA by phosphorothioate and phosphorodithioate DNA. SK-BR-3 cells were treated with antisense US-1 (SEQ. ID NO:1) or scrambled control US-D (SEQ. ID NO:6) in both the full monothioate (S) or alternating dithioate (S2O2) configuration for 24 hours. Cells were then sorted based upon content of the fluoresceinated tracer and the RNA extracted. Ten µg of total RNA from each sample was probed with an erbB-2 cDNA. The blot was stripped and rehybridized with a probe for the GAPDH gene. After densitometry through three different points of the hybridizing bands, normalization to the GAPDH signal shows that a 5–10 fold reduction in erbB-2 mRNA is achieved by both of these compounds in the high fluorescent window, consistent with protein data (FIG. 1) and an RNaseH mode of action.

The alternating dithioate (S2O2) US-1 sequence (SEQ ID NO:1) appeared to work as well as the all monothioate sequence (S) as measured by the decrease in steady-state levels of the erbB-2 protein. In order to confirm that these compounds were specifically inhibiting erbB-2 mRNA, we used the fluorescent tracer compound and flow cytometry to physically sort cells 24 hours after lipofection into low and high fluorescent fractions. Total cellular RNA extracted from these cells was hybridized with an erbB-2 cDNA probe followed by a probe for the GAPDH gene to control both for RNA loading and non-specific inhibition of RNA levels (data not shown). Hybridization to erbB-2 was quantitated and normalized to the signal for GAPDH (FIG. 2). Specific and potent inhibition of the erbB-2 mRNA was seen in the high fluorescent fraction for both the US-1 (SEQ ID NO:1) S2O2 and S sequences compared to both the low fluorescent fractions and to the high fluorescent fraction of the scrambled control sequences (US-D; SEQ ID NO:6). The alternating dithioate yielded approximately a 10-fold reduction compared to a 5-fold reduction in erbB-2 mRNA achieved by the all monothioate antisense compound. This experiment indicates that the S2O2 backbone can specifically inhibit an RNA target, likely through the activity of RNase H, with at least the same efficiency as the all monothioate sequence.

EXAMPLE 7

Effect of sequence variations

Figure 3:
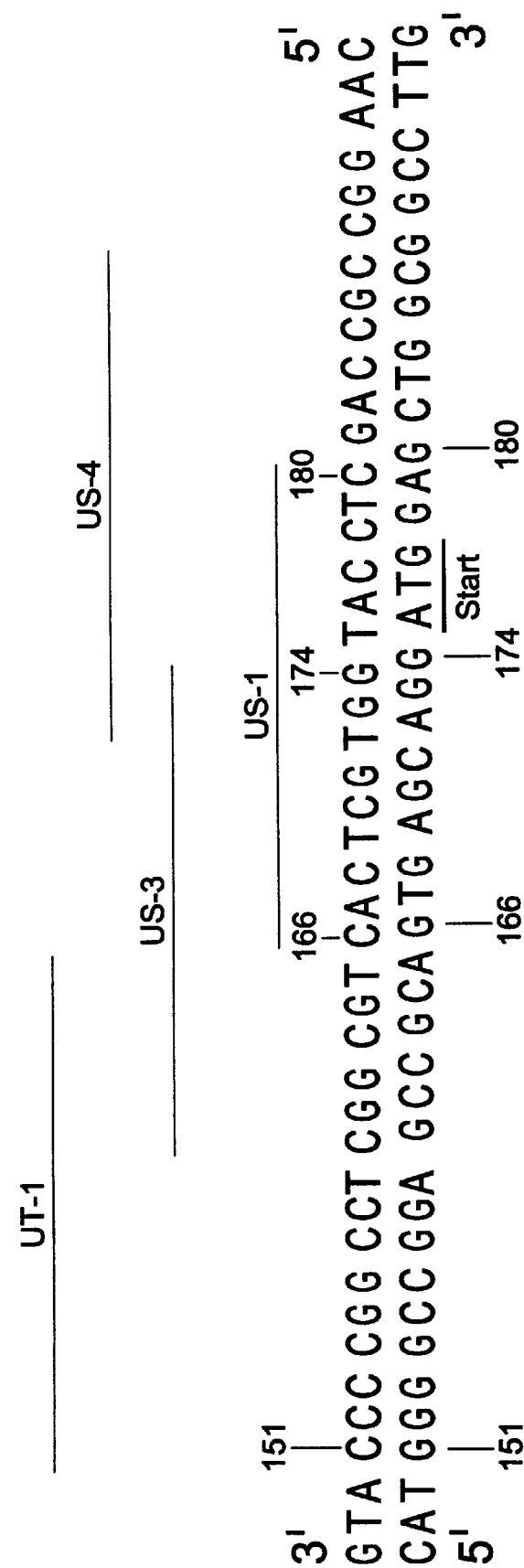
FIG. 3: Position of the different erbB-2 specific antisense sequences (SEQ ID NO:1 through SEQ ID NO:5) in relation to the start of translation.
Figure 4:
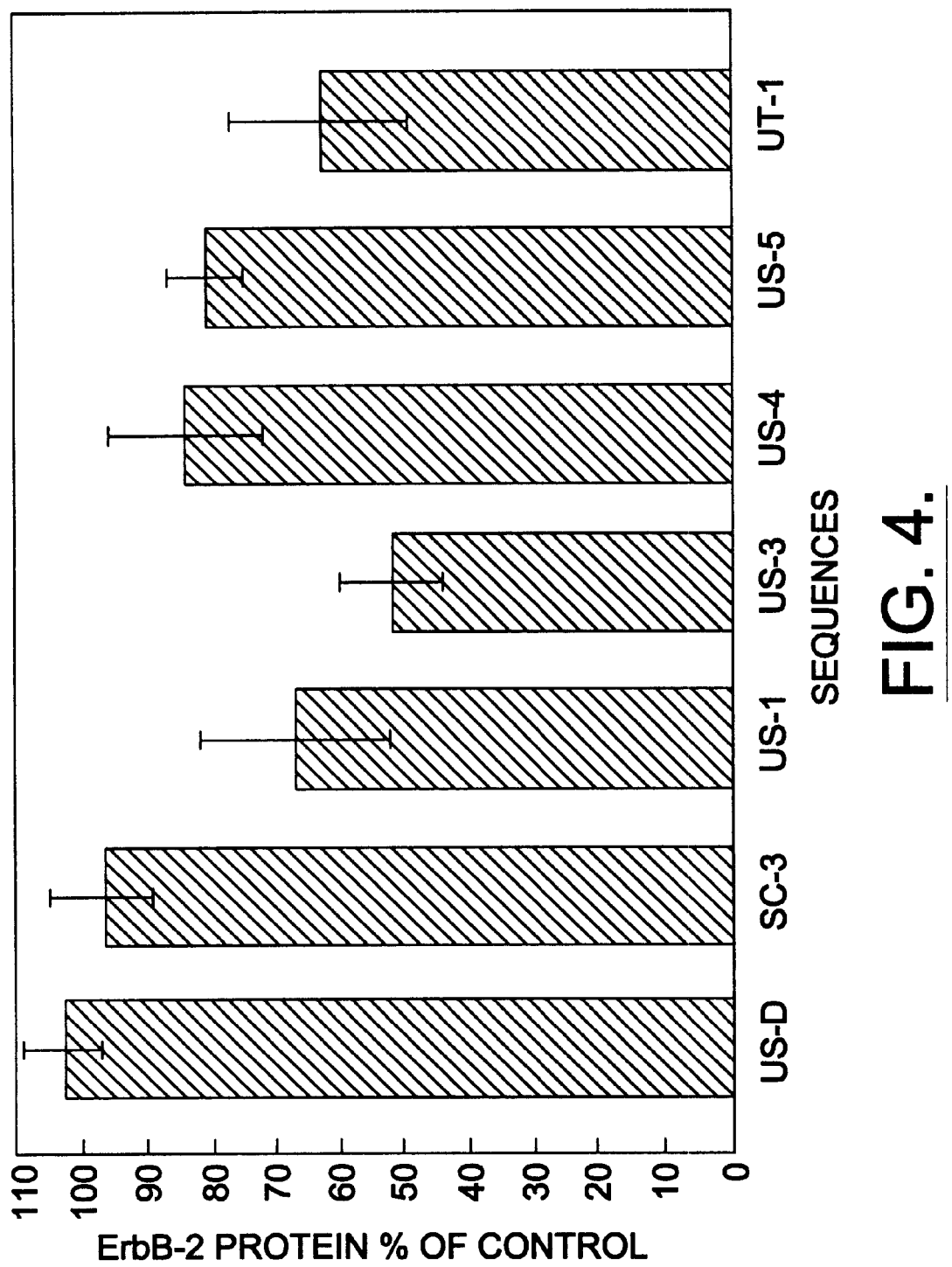
FIG. 4: Two-color flow cytometric analysis of the different erbB-2 specific antisense sequences shown in FIG. 3. Flow cytometry was carried out with the same parameters as in FIG. 1. All sequences are full monothioates with US-D (SEQ ID NO:6) and SC-3 (SEQ ID NO:7) being scrambled controls of US-1 (SEQ ID NO:1) and U S-3 (SEQ ID NO:2) respectively. Quantitation of erbB-2 in triplicate cultures treated with different anti-erbB-2 sequences. The values are presented as a percentage of the combined mean for the two control sequences, US-D (SEQ ID NO:6) and SC-3 (SEQ ID NO:7).

The US-1 (SEQ ID NO:1) sequence is 15 bases long and targets the start of erbB-2 translation (Table 1 and FIG. 3). This sequence was chosen from an initial series of sequences that included the start of transcription and the intron 1 splice donor and acceptor sites as other targets. Extensive testing of the US-1 sequence (SEQ ID NO:1) showed that it consistently inhibited the steady-state levels of erbB-2 and led to an accumulation of cells in the Gi phase of the cell cycle (J. Vaughn et al., *supra*). We systematically shifted the target upstream and downstream (in 3 base increments, all monothioates) in an effort to improve the antisense effect (SEQ ID NO:2 through SEQ ID NO:5; Table 1 and FIG. 3). This series of sequences was tested in triplicate lipofections and compared to US-1 (SEQ ID NO:1) by flow cytometry in SK-BR-3 cells (FIG. 4). Each of the antisense sequences inhibited erbB-2 protein levels but with widely varying potency. The two compounds that target sequences 5' of US-1 (US-3, SEQ ID NO:2, and UT-1, SEQ ID NO:5) were more efficient than the 3' targets (US-4, SEQ ID NO:3, and US-5, SEQ ID NO:4) The flow cytometric analysis yields a dose response curve in a single step, i.e., erbB-2 levels and the amount of fluorescent tracer are measured on a per cell basis. Downregulation at lower tracer levels is indicative of more effective antisense compounds. In particular, the US-3 (SEQ ID NO:2) sequence achieved more erbB-2 inhibition than US-1 (SEQ ID NO:1) and at a lower dose. This can be seen in the flow analysis with more cells having a decreased erbB-2 content (Y-axis) at lower X-axis values. This result was highly reproducible in a number of different experiments. The UT-1 SEQ ID NO:5 sequence performed slightly better than US-1 (SEQ ID NO:1) as well. The relative activity of the US-3 (SEQ ID NO:2) versus US-1 (SEQ ID NO:1) sequences was also compared in another erbB-2 gene amplified cell line, SK-OV-3 derived from an epithelial ovarian cancer. Similar results were obtained with US-3 (SEQ ID NO:2) having greater antisense activity than US-1 (SEQ ID NO:1) (data not shown).

To further characterize and compare the relative efficiencies of the US-1 (SEQ ID NO:1) and US-3 (SEQ ID NO:3) sequences, we measured their effects on de novo erbB-2 protein synthesis at varying doses. SK-BR-3 cells were lipofected with the antisense compounds, US-1 or US-3 (SEQ ID NO:1) (and their cognate scrambled controls; US-D (SEQ ID NO:6) and SC-3 (SEQ ID NO:1) respectively). At 12 hours after lipofection, the cells were labeled for 1 hour with $^{35}$S-methionine. Protein extracts were prepared and an immunoprecipitation performed using both an anti-erbB-2 and an anti-proliferating cell nuclear antigen (PCNA) antibody (data not shown). Phosphorimage quantitation of the specifically immunoprecipitating bands was obtained and the erbB-2 signal was normalized to the level of PCNA in each lane. This ratio was then compared to the erbB-2:PCNA ratio obtained using the scrambled control compounds (expressed as percent of control in FIG. 5). While US-1 (SEQ ID NO:1) was only effective at 0.3 μM (the dose used in all previous experiments), US-3 (SEQ ID NO:2) continued to inhibit erbB-2 protein synthesis at the lowest concentration used (0.075 μM). This is consistent with the flow cytometric data that also indicated US-3 (SEQ ID NO:2) was effective at lower doses, i.e., at lower intracellular tracer concentrations.

The foregoing examples are illustrative of the present invention, and are not to be construed as limiting thereof. The invention is defined by the following claims, with equivalents of the claims to be included therein.

That which is claimed is:

1. An oligonucleotide consisting of the nucleotide sequence:

GGT GCT CAC TGC GGC (SEQ ID NO:2); or

TGC GGC TCC GGC CCC (SEQ ID NO:5).

2. An oligonucleotide consisting of the nucleotide sequence:

GGT GCT CAC TGC GGC (SEQ ID NO:2).

3. An oligonucleotide consisting of the nucleotide sequence:

TGC GGC TCC GGC CCC (SEQ ID NO:5).

* * * * *

UNITED STATES PATENT AND TRADEMARK OFFICE
CERTIFICATE OF CORRECTION

PATENT NO. : 5,910,583
DATED : June 8, 1999
INVENTOR(S) : Jeffrey R. Marks, James P. Vaughn, James D. Iglehart It is certified that error appears in the above-indentified patent and that said Letters Patent is hereby corrected as shown below:

ON the title page item [75] inventors:

please change "Inglehart" to -- Iglehart --.

Column 8, line 53, please insert -- , -- after "(US1".

Column 10, line 28, delete "NO:3" and insert -- NO:2 --.

Column 10, line 31, after "US-1" please insert -- (SEQ ID NO:1) --

Column 10, line 31, after "US-3" please insert -- (SEQ ID NO:2) --.

Column 10, line 32, please delete "(SEQ ID NO:1)".

Column 10, line 33, please delete "NO:1" and insert -- NO:7--.

Signed and Sealed this

Twentieth Day of March, 2001

Attest:

NICHOLAS P. GODICI

*Attesting Officer*  *Acting Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 15 base pairs
      (B) TYPE: nucleic acid (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:1:

CTCCATGGTG CTCAC                                                        15

(2) INFORMATION FOR SEQ ID NO:2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:2:

GGTGCTCACT GCGGC                                                        15

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:3:

CGCCAGCTCC ATGGT                                                        15

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:4:

CAAGGCCGCC AGCTC                                                        15

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:5:

TGCGGCTCCG GCCCC                                                        15

(2) INFORMATION FOR SEQ ID NO:6:

(i) SEQUENCE CHARACTERISTICS:
        (A) LENGTH: 15 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:6:

CGCCTTATCC GTAGC                                                          15

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:7:

GGTCGATGCC GCGTC                                                          15

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:8:

TCTCTCTCTC TTTTT                                                          15
```